(12) United States Patent
Fernandez et al.

(10) Patent No.: US 8,487,245 B2
(45) Date of Patent: Jul. 16, 2013

(54) DIRECT ATMOSPHERIC PRESSURE SAMPLE ANALYZING SYSTEM

(75) Inventors: Facundo M. Fernandez, Atlanta, GA (US); Glenn A. Harris, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 84 days.

(21) Appl. No.: 13/322,687

(22) PCT Filed: May 28, 2010

(86) PCT No.: PCT/US2010/036652
§ 371 (c)(1),
(2), (4) Date: Nov. 28, 2011

(87) PCT Pub. No.: WO2011/025564
PCT Pub. Date: Mar. 3, 2011

(65) Prior Publication Data
US 2012/0068063 A1     Mar. 22, 2012

Related U.S. Application Data

(60) Provisional application No. 61/181,735, filed on May 28, 2009.

(51) Int. Cl.
*H01J 49/10* (2006.01)
*H01J 49/26* (2006.01)

(52) U.S. Cl.
USPC ........ 250/288; 250/281; 250/282; 250/423 R; 250/424; 315/111.21

(58) Field of Classification Search
USPC ...... 250/288, 281, 282, 423 R, 424; 315/111, 315/21
See application file for complete search history.

(56) References Cited

U.S. PATENT DOCUMENTS

| | | | |
|---|---|---|---|
| 7,429,731 B1 * | 9/2008 | Karpetsky | 250/288 |
| 8,173,959 B1 * | 5/2012 | Boumsellek et al. | 250/288 |
| 2011/0036977 A1 * | 2/2011 | Denton et al. | 250/283 |

* cited by examiner

*Primary Examiner* — Nikita Wells
(74) *Attorney, Agent, or Firm* — Ryan A. Schneider, Esq.; Troutman Sanders LLP

(57) ABSTRACT

A system, method and apparatus for injecting reactive species and ions from an ambient plasma ionization source into an atmospheric pressure ion mobility spectrometer.

26 Claims, 12 Drawing Sheets

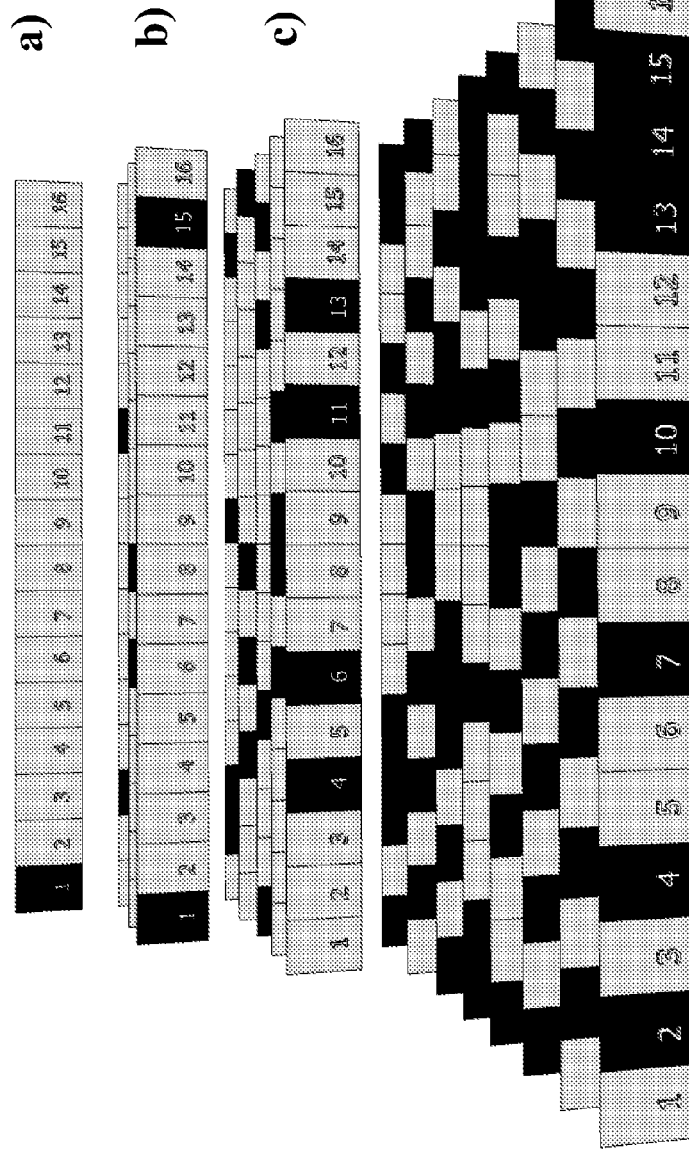

DIRECT ATMOSPHERIC PRESSURE SAMPLE ANALYZING SYSTEM

CROSS-REFERENCE TO RELATED APPLICATIONS

This application is a US National Stage of International Application No. PCT/US2010/036652, filed 28 May 2010, which claims the benefit of 61/181,735, filed 28 May 2009.

BACKGROUND OF THE INVENTION

1. Field of the Invention

The present invention is directed towards a sample analyzing system, and more particularly to a system, method and apparatus for injecting reactive species and ions from an ambient ionization source into an atmospheric pressure ion mobility spectrometer.

2. Description of the Related Art

In order to address current and future chemical vapor and aerosol threats to homeland security, chemical detection systems should be versatile and robust to identify hazardous chemicals ranging from traditional chemical warfare agents (CWA) to toxic industrial compounds (TIC). Instruments should operate in an efficient, easy, and safe manner so that trained users can obtain reliable and reproducible readings. Instruments should be flexible to meet changing homeland security goals for chemical analysis, and in particular, have the ability to be portable aiding first responders with the identification of any unknown toxins in the event of a serious industrial accident exposing workers to TICs or public exposure to CWAs from a terrorist attack.

Detection technologies including chemical sensor arrays, electrophoresis-based lab-on-a-chip devices, impedance measurements with modified carbon nanotubes, piezoresistive microcantilevers, and micro gas analyzers have been shown to be potential fieldable technologies capable of chemical agent detection.

Solid phase microextraction (SPME) coupled to gas chromatography (GC), fast GC, and liquid chromatography (LC) are also common approaches to detection of CWAs and TICs in both laboratory and field environments.

Additionally, low ppb detection limits and rapid response of ion mobility spectrometry (IMS) has been shown to be a very useful tool for the detection of CWAs and TICs. Thousands of portable IMS units have been distributed throughout the world associated with aviation security against explosives and battlefield detection of CWAs.

IMS instruments often use a radioactive ionization source (e.g. $^{63}$Ni) emitting β-electrons due to its simplicity and reliable performance. However, procedural requirements involving the licensing, placement, use, and disposal of these instruments incur additional costs and regulations. Electrospray, corona and glow discharges, laser, X-ray, and photo ionization techniques are other common ionization techniques used for IMS.

The emergence of new ambient ionization techniques has led to an explosive growth in new applications and methodologies for mass spectrometry (MS) experiments. Largely absent from these advances has been the coupling of ambient ionization techniques to IMS. To date, only the ambient ionization technique desorption electrospray ionization (DESI) has been coupled to reduced pressure IMS for the analysis of pharmaceuticals, peptides, and proteins. One of the primary reasons for this is the difficulty in transporting ambiently-generated ions against an uphill electric field at the entrance of an atmospheric pressure (AP) IMS instrument. Utilization of reduced pressure of ion traps, funnels, or optics to pump ions into the instrument before entering an IM cell within the instrument has been examined.

Known prior art includes US Patent Publications 2008/0173809 to Wu, 2005/0205775 to Bromberg et al., 2008/0121797 to Wu, and U.S. Pat. No. 5,192,865 to Zhu. US Patent Publication 2008/0173809 to Wu discloses that simply placing a plasma ion source in front of the inlet to the ion mobility instrument will be sufficient for efficient ion transmission into the instrument and subsequent ion mobility analysis. However, as one of skill in the art understands, this will only work under two conditions: 1) if the gas velocity flux leaving the ion source is greater than the magnitude of the upfront electric field present at the entrance of the instrument; and/or 2) the ion source is held at a higher floating potential than the entrance electrode of the ion mobility instrument. With one or both of these operating principles, it would be theoretically possible to ionize and effectively transport ions from outside of the entrance electrode of the ion mobility spectrometer to inside it for separation.

Bromberg et al. uses a plasma based ionization technique for ion mobility spectrometry (IMS). Particular mention in Bromberg et al. is spent on the separate placement of an electron beam source, such as a corona discharge, from within the instrument. A window, such as made from diamond or sapphire, allows the electron current to pass into an enclosure region where the sample is held to promote ionization and reduce negative space charging effects.

US Patent Publication No. 2008/0121797 to Wu discloses the use of a sampling substrate, such as a porous media. In 2008/0121797 to Wu, a vapor preconcentrator is used to concentrate desorbed species, which can then be rereleased into an extraction zone for ionization.

Zhu outlines the use of an atmospheric pressure afterglow discharge source coupled to a charged ion detector. However, the implementation as outlined in Zhu focuses on nebulized samples and a solvent return system for sampling in the afterglow region of the source. As outlined in Zhu sampling intact samples could not be possible without interference of the plasma-flux stability since ion/electron charge densities would be in a state of constant flux. Further, the afterglow plasma ion source of Zhu cannot be implemented outside a standalone ion mobility spectrometer since the electric field bias on the ion source would need to be higher than the entrance electrode on the ion mobility spectrometer.

Thus, a need exists for a system using direct in-situ ionization within the electric field gradient of a drift tube (DT) atmospheric pressure IMS instrument to enhance sensitivity, improve ion transport, and provide a safe sampling strategy.

BRIEF SUMMARY OF THE INVENTION

The present invention comprises a system that marries open-air plasma ionization techniques, commonly called ambient plasma ionization techniques, in particular, metastable and reactive species generating—ambient ionization techniques such as, among others, Direct Analysis in Real Time (DART), Flowing Atmospheric Pressure Afterglow (FAPA), and Low Temperature Plasma probe (LTP) to ion mobility spectrometry (IMS).

In a preferred embodiment, the present invention comprises a system using direct in-situ ionization within the electric field gradient of a drift tube (DT) atmospheric pressure IMS instrument to enhance sensitivity, improve ion transport, and provide a safe sampling strategy. In exemplary embodiments, a direct analysis in real time (DART) ionization source is used for this coupling due to its generation of uncharged but highly energetic metastable species which could be injected directly into an electric field where the sample is placed.

DART, FAPA, LTP, and other ambient plasma ionization techniques have attracted significant attention due to their high-throughput analysis capabilities and straightforward operation. When coupled to mass spectrometry (MS) ambient plasma ionization generated ions can be mass analyzed for identification. Unfortunately, field portable mass spectrometers are still in the initial stages of development, whereas atmospheric pressure drift tube ion mobility spectrometry (DTIMS) has been successfully deployed in a wide variety of field scenarios.

In atmospheric pressure DTIMS ions are separated according to their ionic mobility in a time-invariant electric field while drifting against a flow of drift gas. An ambient plasma-based ionization atmospheric pressure DTIMS platform offers an easy-to-use, low maintenance chemical agent monitoring system.

The present invention can comprise a sample analyzing system including a plasma ionization source configured to ionize an analyte sample under ambient pressure, an ion mobility spectrometer configured to operate under ambient pressure, wherein the ion mobility spectrometer comprises an inlet, an ionization region, a ion separation region, and some type of detector, arranged such that the ionization region is downstream of the inlet, the ion separation region is downstream of the ionization region, and the detector is downstream of the ion separation region, and a sample transport assembly configured to transport the analyte sample through the inlet of the ion mobility spectrometer and to the ionization region, wherein the sample transport assembly is in physical communication with the plasma ionization source, wherein the analyte sample is ionized in the ionization region of the ion mobility spectrometer, and wherein an electric field at the inlet of the ion mobility spectrometer is greater than an electric field produced by the plasma ionization source when both the ion mobility spectrometer and the plasma ionization source are activated.

The sample transport assembly can comprise a sample platform configured to hold the analyte sample, and a tube comprising a first end comprising an inlet and a second end comprising an outlet, wherein the first end of the tube is in physical communication with the plasma ionization source, and wherein the second end of the tube is in physical communication with the sample platform.

The sample platform can be porous, beneficially facilitating transport of a liquid, gaseous, or aerosol analyte sample into the ionization region of the ion mobility spectrometer.

The porous sample platform can comprise a sorbent material for holding the liquid, gaseous, or aerosol analyte sample, and can be at least partially formed from an electrically conductive material.

The at least partially electrically conductive porous sample platform can be positioned at the inlet or within the ionization region of the ion mobility spectrometer effective to permit the electric field of the ion mobility spectrometer to travel through the electrically conductive porous sample platform such that the inlet comprises at least a portion of the ionization region.

In another exemplary embodiment of the present invention, a method of analyzing a sample is disclosed, the method comprising providing an ion mobility spectrometer comprising an inlet, an ionization region, a ion separation region, and a detector, arranged such that the ionization region is downstream of the inlet, the ion separation region is downstream of the ionization region, and the detector is downstream of the ion separation region, introducing an analyte sample into the ionizing region of the ion mobility spectrometer, ionizing the analyte sample within the ionizing region of the ion mobility spectrometer, wherein the ionization occurs under ambient pressure via a plasma ionization source, separating ions of the ionized analyte sample under ambient pressure within the ion separation region, and detecting at least a portion of the ions under ambient pressure with the detector of the ion mobility spectrometer, wherein an electric field at the inlet of the ion mobility spectrometer is greater than an electric field produced by the plasma ionization source when both the ion mobility spectrometer and the plasma ionization source are activated, and wherein both the plasma ionization source and the ion mobility spectrometer are not activated when the analyte sample is introduced into the ionizing region of the ion mobility spectrometer.

The sample introduction step can be accomplished using a sample transport assembly, wherein the sample transport assembly is in physical communication with the plasma ionization source.

The analyte sample can comprise more than one chemical constituent, such that ionizing the analyte sample comprises ionizing two or more of the chemical constituents, and separating ions of the ionized analyte sample comprises separating ions of two or more of the chemical constituents, and detecting at least the portion of the ions comprises detecting at least a portion of the ions of the two or more ionized chemical constituents.

Each of the more than one chemical constituents can be ionized simultaneously or in a time-resolved fashion.

The at least a portion of the two or more ionized chemical constituents can be detected at a different time.

In another exemplary embodiment, the present invention comprises an ambient analyte identification process comprising providing an ion mobility spectrometer with an inlet and a reaction region in a drift tube, applying an electric field at the inlet of the ion mobility spectrometer, placing a sample through the inlet, and into the reaction region of the ion mobility spectrometer, and ionizing the sample in the reaction region of the ion mobility spectrometer with an ambient plasma ionization source, wherein the ions travel through the drift tube which has the applied electric field and a carrier buffer gas that opposes the ions' motion, and wherein a detector in proximity to a distal end of the drift tube can distinguish different analyte species based on an ions' mass, charge, size and shape, such that the migration time through the tube is characteristic of different ions.

Ionization of the sample can occur in-situ within the electric field gradient of the ion mobility spectrometer. Ionization of the sample can provided by an ambient plasma ionization source. The drift tube can comprises monolithic resistive glass.

Placing a sample through the inlet, and into the reaction region of the ion mobility spectrometer can comprise mounting the sample and a reagent gas transfer tube on a movement system, wherein the reagent gas transfer tube both holds the sample, and hydro-dynamically focuses the gas plume from the ambient plasma ionization source onto the sample, facilitating efficient ionization of surface bound species.

The movement system can comprise a rail system external the ion mobility spectrometer allowing for safe, repeatable and reproducible placement of the sample into the reaction region of the ion mobility spectrometer.

In another exemplary embodiment, the present invention comprises a sample analysis system comprising an ambient plasma ionization source, an ion mobility spectrometer located distal the ambient plasma ionization source, the ion mobility spectrometer having an inlet and a reaction region, and an ambient transport assembly to transfer ions from the ambient plasma ionization source to the reaction region of the ion mobility spectrometer.

In another exemplary embodiment, the present invention comprises a method of sample analysis comprising generating ions with an ion generator at a first electric potential, injecting the ions from the ion generator into the ion measurement device, and identifying the ions with an ion measurement device at a second electric potential, wherein the first electric potential is lower than the second electric potential, and wherein since the first electric potential is lower than the second electric potential, injecting the ions from the ion generator to the ion measurement device occurs.

An object of the present invention is to provide a system, method and apparatus for injecting reactive species and analyte ions from an ambient ion source into an IMS. This embodiment is exemplified with a plasma-based ambient ion source where ions are to be injected from a low or null electrical field region into a high field region such as generation of ions by an ionization technique at a lower electric potential than the instrument.

Another object of the present invention is to provide a system, method and apparatus that can directly sample solids, liquids and gases/aerosols within the high electric field region of the IMS (in-situ ion generation) or of an externally-generated electrical field outside of the opening entrance of the IMS extending as far away as the ambient ionization source.

The present invention provides ways of interfacing an ambient plasma based ionization technique such as direct analysis in real time mass spectrometry (DART) with an ion mobility spectrometer/separator. The present invention demonstrates and details the precise coupling of a plasma ion source such as DART to an ion mobility instrument.

The present invention is patentably distinct from US Patent Publication 2008/0173809 to Wu at least as to alternative methods to circumvent excessive gas flow rates and/or electric fields. For example, the present invention maintains the normal operating conditions of the ionization source (gas flow rates<6 L/min, discharge $V_{dc}$<5 kV) so that typical home-built and commercial ionization sources can be interfaced to ion mobility instruments with little to no modification. This is done by, for example, passively ionizing samples in-situ (within) the instrument itself in a desolvation/reactive drift tube prior to the ion gating mechanism, such as a Bradbury-Nielsen ion gate/shutter, providing the advantage of not needing to modify the ion source settings. This is demonstrated by an extended gas nozzle that goes from the plasma ion source exit to the entrance electrode and in some cases inside the reactive drift tube of the ion mobility instrument itself. This approach can be accomplished with the electric field of the ion source and ion mobility instrument on or off.

The present invention also demonstrates a transmission-mode geometry in which an extended gas nozzle is not required, but can still be used such that the sample is deposited on a conductive perforated material, such as a steel mesh, which is held at a potential higher or at the same as the entrance electrode bias of the ion mobility instrument. Since ionization occurs at the origin of the applied electrical field, this can again be classified as in-situ ionization, but different from the above method in that the sample is positioned farther away from the ion gate by not being within the reactive drift tube. Both approaches utilize uncharged energetic metastable species produced by the plasma ion source and not ions produced by the plasma ion source. Therefore, the metastables can travel into the ion mobility instrument without high gas velocity or electric field assistance as required in an implementation outlined in US Patent Publication 2008/0173809 to Wu.

Unlike Bromberg et al., the present invention preferably filters out any of the primary charged particles (electrons, ions) produced by the plasma ion source utilizing only neutral gas molecules and neutral metastable species. These chemical species are neither composed in an accelerated beam nor a pulsed beam as described in Bromberg et al. They are simply emitted from the plasma ion source and can be hydrodynamically focused with gas nozzles of varying geometries. Sampling with the present invention is enclosureless in both the passive and transmission-mode geometries, unlike Bromberg et al. Ions formed in the present invention do not need to be preconcentrated as shown in Bromberg et al. Additionally, timing of the ion shutter grid is independent of both the applied ion mobility and ion source voltages, unlike Bromberg et al.

The present invention is patentably distinct from US Patent Publication No. 2008/0121797 to Wu in that an applied voltage is placed on the sample holder and/or transmission-material to improve ion dynamic focusing and transport. In 2008/0121797 to Wu, it is never specified or implied that the sample substrate is in contact with gas originating from a plasma ionization source, such as the gas jet exiting an ambient plasma source. Additionally, the present invention does not require a chemical coating. The nature of coating used in the present invention is an inert derivative of graphitized black, which is not disclosed in 2008/0121797 to Wu.

Additionally, unlike 2008/0121797 to Wu, the present system allows for both passive offline analysis of gases, liquids, aerosols, suspensions and powders to be collected and tested or the direct application of similar samples to the transmission material without the use of artificial purging of gases into the preconcentration region. Direct application can be accomplished via automated, robotic, human or other manual supervised or unsupervised method.

The transmission material and substrate of the present system allows for heating via heated gas, contact with the heated ion mobility instrument and direct application of a current to a conductive transmission material. No additional sample ports for ion sources are required for interfacing to other ionization sources since our system is standalone. Further, the sample holder is not sealed in our implementation and is inert, free from chemical modification. It is used only to hold a preferred sample like a solid or a transmission material such as a screen mesh.

Unlike Zhu, a present method removes the implementation of plasma ionization sources, in particular ambient sources, with a charged ion detector (in one case, an ion mobility spectrometer), and therefore, it can sample solids and liquids via neutral sputtering or thermal desorption. As discussed, Zhu cannot sample intact samples without interference of the plasma-flux stability since ion/electron charge densities would be in a state of constant flux. The present invention can remove such effects by utilizing ionization processes via the interaction of neutral metastable species directly with the samples and/or interaction of neutrals via Penning ionization with other species that can then ionize the sample. Further, unlike Zhu, the plasma source of the present invention can be operated at any conditions away or connected to the instrument by using the disclosed method for coupling and injection of metastable species to and within the entrance of the ion mobility instrument where the intact sample is placed for in-situ analysis.

Other aspects and features of embodiments of the present invention will become apparent to those of ordinary skill in the art, upon reviewing the following detailed description in conjunction with the accompanying figures.

BRIEF DESCRIPTION OF THE FIGURES

The various embodiments of the invention can be better understood with reference to the following drawings. The components in the drawings are not necessarily to scale, emphasis instead being placed upon clearly illustrating the principles of the various embodiments of the present invention. In the drawings, like reference numerals designate corresponding parts throughout the several views.

FIGS. 9a-9d illustrate multiplexing with IMS, according to an exemplary embodiment of the present invention.

DETAILED DESCRIPTION OF PREFERRED EMBODIMENTS

Figure 1:
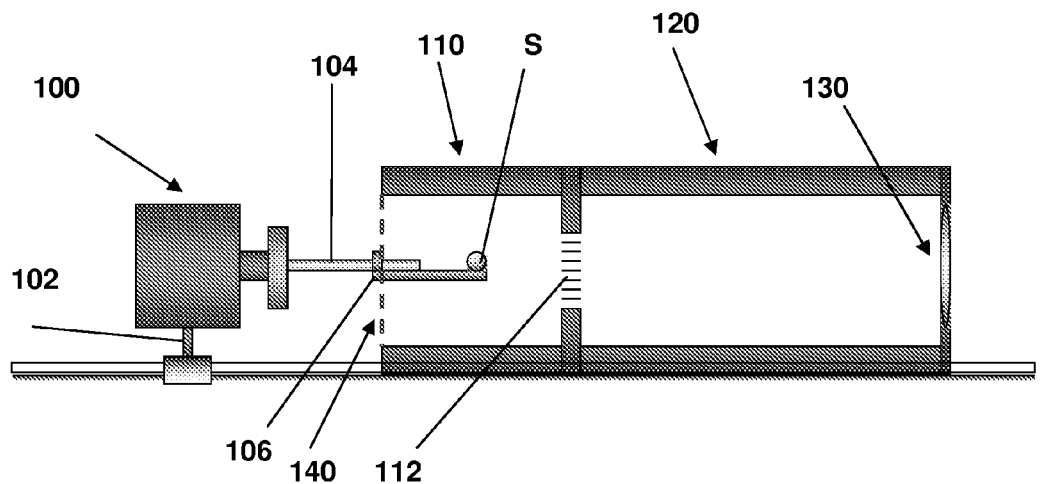
FIG. 1 illustrates a cross-sectional view of the DART-IMS interface according to an exemplary embodiment of the present invention.

Although preferred embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

FIG. 1 illustrates cross-sectional depiction of the DART-IMS interface of a preferred embodiment of the present invention. The interface comprises a DART or other plasma type ion source 100, height and longitudinal adjustable rail 102, hydrodynamic gas transfer tube sample holder with rotational and longitudinal adjustable collar 106 IMS reaction chamber 110 (high voltage), sample S (solid tablet shown here), pulsed ion gate 112, IMS drift tube 120 (high voltage), ion detector 130 (low voltage), and a perforated grid to enhance ion transmission 140.

A conventional DART-type ion source 100 can modified by coupling a reactive gas transfer tube 104 to the ion source gas outlet that extends into the high electrical field. The reagent gas transfer tube 104 can simultaneously serve as a support for the sample S. The transfer tube 104 is optimally made of a chemically inert material (e.g. glass) that will not ionize due to collisions with the metastable and other reactive species formed by the ionization source. This tube 104 may be thermally resistive (e.g. ceramic) or externally heated to maintain the reactive gas temperature of the species exiting the heated region of the ionization source. Tube 104 may also be electrically conductive (e.g. stainless steel or resistive glass) to extract ions from the metastable reactive stream before contacting the sample and to produce a secondary higher electrical field in addition to the electrical field generated from the DART and IMS.

The gas transfer tube 104 focuses the reactive gas plume onto the sample S, facilitating efficient ionization of surface bound species by mechanisms such as chemical sputtering or surface ionization (e.g. surface Penning-ionization). In addition, the reactive gas stream and/or the IMS instrument may be heated to facilitate thermal desorption of neutral analytes from the sample matrix. Desorbed analytes would then be ionized by the reactive gas plume that exits the gas transfer line via chemical ionization pathways (e.g. Penning, charge-exchange, and proton-transfer pathways).

Mounting the ion source and the transfer tube on a moveable rail system 102 external to the ion mobility instrument allows the assembly to be reproducibly inserted into and out of the IMS drift tube high electric field. For improved ion transmission, an electrically-conductive grid 112 can be either (a) mounted on the sample holder so it electrically contacts the spectrometer inlet when the sample is placed in position, or (b) furnished with a small perforation and mounted directly on the IM spectrometer entrance so the transfer tube can slide through it when inserted.

Figures 2A, 2B:
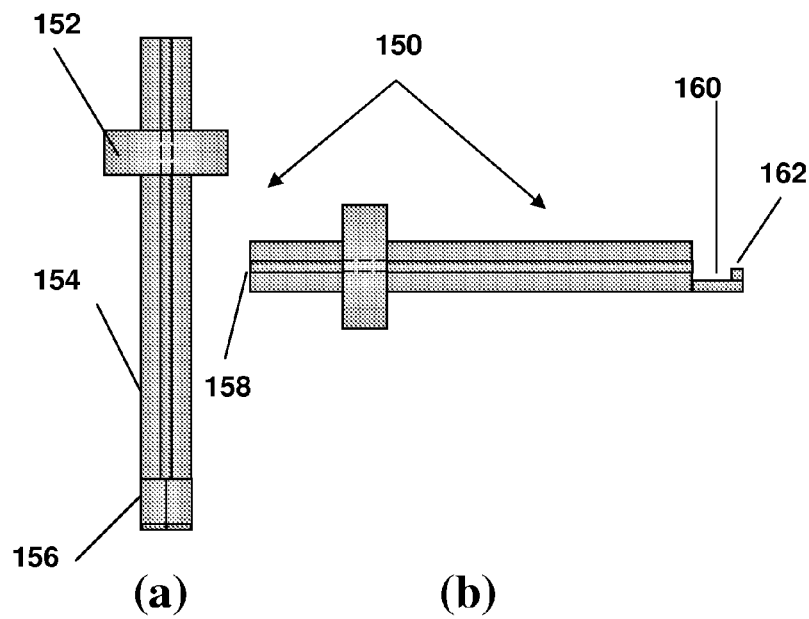
FIGS. 2a-2b are a top and side view, respectively, of a sampling tube with sample holder collar according to an exemplary embodiment of the present invention.

The sampling tube 104 can be furnished with the sample holder collar 106 that can be custom built for solids (as shown in FIGS. 2a and 2b) or be as simple as a holder for supporting melting point glass capillaries for liquids. A combined DART-IMS custom transfer tube/sample holder 150 can comprise an adjustable (rotational and transverse) collar 152, a non conductive gas tube support sleeve 154, a sample stage 156, gas transfer tube inlet 158, a gas transfer tube outlet 160, and a sample support lip 162.

This sample holder/sampling tube assembly 150 facilitates precise sample placement within the drift tube maximizing detection sensitivity and reproducibility. Gas/aerosol samples may be analyzed by pumping or directing the gas such that it interacts with the reactive gas exiting into the instrument or by collection onto appropriate grids mounted on the above described interface.

Figures 3A, 3B:
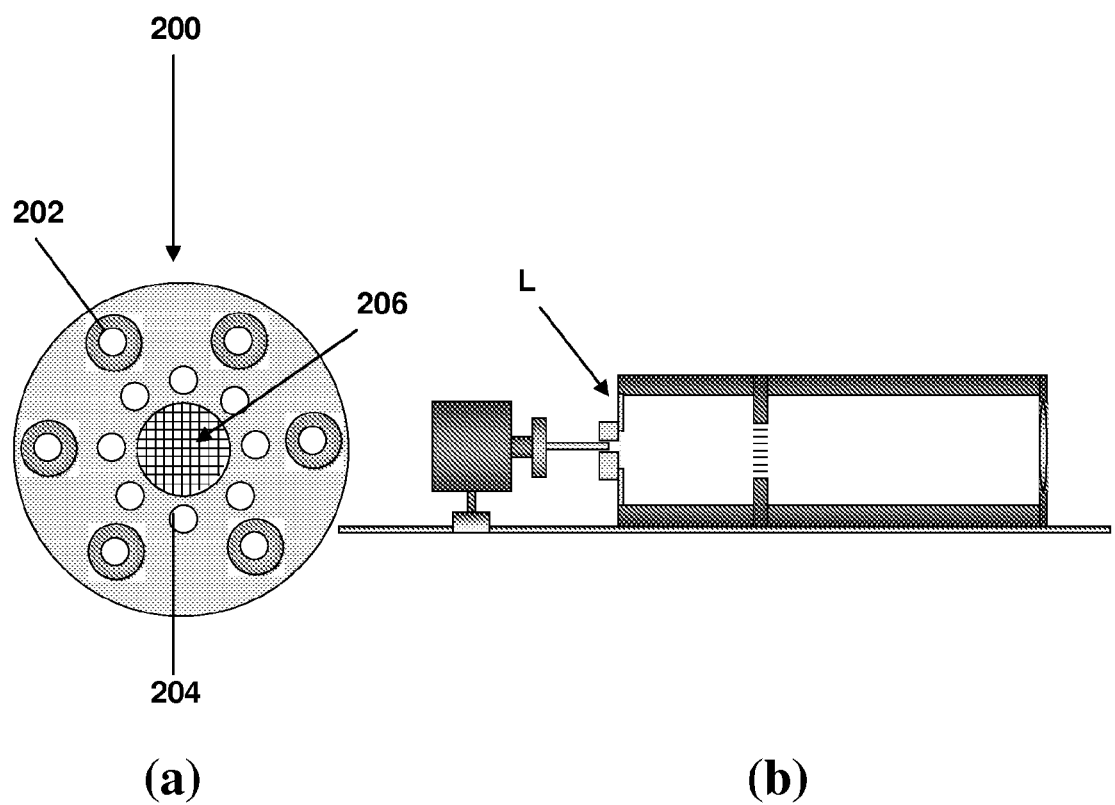
FIGS. 3a-3b are a front view a sorbent screen mesh assembly, and its location in the setup, respectively, according to an exemplary embodiment of the present invention.

Liquids and gases/aerosols may be extracted and/or pre-concentrated onto premade porous materials, screens, meshes or fibers with a sorbent coating removing the need of external gas pumping into the instrument and improving sensitivity (FIG. 3). The sorbent screen mesh or fiber holder assembly 200 can connect to the front of the IMS via screws 202 for easy removal, and can include vent holes 204 to allow gas to leave the instrument, while the sorbent material 206 is placed in the middle of the assembly 200 to allow for transmission-mode analysis. Location L illustrates the screen-supporting assembly 200 mounted on the IM spectrometer.

Sorbent screens, meshes and fibers can be mounted internally of the instrument in much the same way as solids. If the sorbent materials are mounted external to the instrument they are positioned directly in front of the reactive gas stream in a "transmission-mode" geometry with a custom sample holder to mount to any IMS. With a transmission-mode orientation the reactive gas stream will pass through the analyte embedded material to allow for ionization of the absorbed material without major disruptions in the gas flow. If the sorbent substrate (mesh or fiber) are electrical conductors (e.g. metal) an electrical potential may be applied to them to allow for ions to be directed into the drift tube of the IMS. In this case, a separate electrical grid at the entrance may be avoided. This electrical potential may be higher or the same as the potential at the entrance of the IMS to facilitate the best electrical field for sampling.

The present set-up allows for ion losses to be minimized by forming analyte ions in-situ within an electrical field generated solely or in part by the IMS, mitigating ion-ion recombination, minimizing neutralization of ions upon formation within the drift tube, and maximizing ion trajectories toward the IMS gate and drift tube.

Safety is improved by placing the sampling system on a moveable assembly that can enter and exit the instrument for tuning, cleaning, and sample placement away from the high field regions when not in operation. These simple assemblies can take many forms, but can implement moveable rails, tracks, bearings, and collars which can easily slide. After securing the sample to the sample holder, the moveable assembly is introduced into the instrument. Depending on the implementation, the electrical fields can be held constantly on, or rapidly turned on after an optional safety interlock is engaged when actuating the rail system.

Thus, the present invention combines the advantages of atmospheric pressure drift tube ion mobility spectrometry with ambient ionization. The present invention eliminates the requirements of a vacuum, utilizes relatively low power, avoids solvents, and provides controlled ionization. It can analyze samples of any shape and size directly, and is adaptable to vapors, liquids, and solids depending on need (i.e. a "platform").

The present invention can be implemented together with multiplexing approaches for trace analysis when using various discharge gases such as, among others, helium, nitrogen, argon, and air.

In an exemplary embodiment, a DART is being coupled to a non-traditional IMS design that has at least two inventive features: it is fabricated with two sections of resistive glass ("glass tubes") Pb-doped to have a given electrical resistance, and it allows for operation in the "pulse-wait" mode (such as a TOF), or in a more sensitive "multiplexed" mode, where more ions are injected. An advantage of using resistive glass is that the design is safer (no need for exposed high voltage dividers), machining cost is much reduced (no stainless steel to machine), and the instrument is greatly simplified. The system incorporates many beneficial parameters for optimization: ion injection geometry, drift voltage, reaction chamber voltage, DART gas and IMS drift gas flow (magnitudes and directions), gas and chamber temperatures.

In an exemplary method of operation, the sample is introduced as a solid (attached to the end of sampling probe shown next), liquid (continuously through a tube that runs parallel to sampling probe or directly applied to the probe), or as a gas (via a miniature pump or headspace sampling system that feeds into the end of the sampling probe). Ions are generated continuously as sample is supplied, or as a broad pulse if a finite amount of sample is ionized. The ions travel towards an ion gating system (e.g., among others, interleaved set of alternating polarity 20 µm wires, and pulsed electrode). This gate opens and closes for µs injections at a frequency of several Hz. Each one of the µs pulses is the start of a "sweep". Multiple sweeps can be averaged. The ions produced by the plasma source are separated in drift chamber against a countercurrent of gas.

Experiments

Reagents

All reagents were analytical grade, purchased from the same chemical supplier (Sigma-Aldrich, St. Louis, Mo., USA) and used without further purification. Solutions of dimethyl methylphosphonate (DMMP, 97%), 2-Chloroethyl ethyl sulfide (2-CEES, 98%), 2,4-Lutidine (99%), and 2,6-Di-tert-butylpyridine (2,6-DtBP, $\geq$97%) were prepared in pure nanopure water (Barnstead International, Dubuque, Iowa, USA), and methamidophos ($\geq$98%) was prepared in a 50% methanol solution. Concentrations of the solutions are described below but for the initial studies 10% solutions of 2,4-lutidine and 2,6-DtBP in $H_2O$ were used. DART and IMS gas was high purity $N_2$ (99.995% Airgas, Atlanta, Ga.).

Instrumentation

A resistive glass drift tube ion mobility spectrometer was used. The desolvation (12 cm) and drift (26 cm) regions (3 cm i.d., 4 cm o.d.) were constructed out of monolithic resistive glass (PHOTONIS USA, Sturbridge, Mass.) at a 0.45 $G\Omega cm^{-1}$ resistance. A Bradbury-Nielsen-type ion gate was placed between the two drift tubes. When closed, the ion gate applied ±35 V to adjacent wire sets. The drift tubes were wrapped with silicone heating tape (Minco, Minneapolis, Minn.). The tubes were supported in a custom made PEEK mounting assembly. This assembly was mounted within a protective Faraday cage for safe operation and for electromagnetic insulation against interferences. Two grid electrodes were used in this set-up. One was positioned in front of the iridited aluminum plate (2.6 cm diameter) Faraday plate detector (TOFWERK AG, Thun, Switzerland). The other grid electrode was placed at the entrance of the desolation tube and had a 0.5 cm slit in the middle for the DART glass gas tube to pass through (described below). A high-voltage power supply (FUG HCL 14-2000, Magnavolt Technologies, Plattsburgh, N.Y.) was connected to a voltage divider to supply the potentials for the entrances, exits, ion gate and grid electrodes. Drift gas entered the instrument behind the detector plate and was controlled by a precision flow meter (PMR1, Bel-ART/Scienceware, Pequannock, N.J.). Data acquisition and ion gate timing was controlled by in-house developed software coded in LabView 7.0 (National Instruments, Austin, Tex.).

A DART-SVP ionization source (IonSense, Inc. Saugus, Mass., USA) was used for all experiments. The ion source was operated in positive ion mode. The DART gas nozzle was connected to a 15 cm long glass tube (0.15 cm i.d., 0.3 cm o.d.). The glass tube was used to inject nitrogen metastable species directly into the desolation tube. A melting point glass capillary tube where liquid samples were deposited was affixed to the glass tube extending 2 cm past the exit. This entire assembly was easily pulled into and out of the desolvation tube through the open slit on the grid electrode due to the built in rail assembly of the ion source.

Set-Up and Procedure

IMS settings for most experiments were as follows: entrance grid and entrance of desolation tube 12 000 V, 400 µs gate pulse widths, 200 µs data acquisition bins, 400 spectral sweeps averaged per analysis, 150° C. instrument temperature, $N_2$ drift gas at 1 L min$^{-1}$. Each 400 µs gate pulse comprised an element in a n=256 element sequence. For the multiplexing experiments, both 200 µs and 400 µs digital (n=512 and 256, respectively) and Hadamard (n=511 and 255, respectively) gating sequences were used, and were accompanied with a constant 50 µs data acquisition bin. DART settings for all experiments were as follows: positive mode glow discharge, grid voltage +500 V, 2.5 L min$^{-1}$ $N_2$ flow rate, and 400° C. heater temperature.

Figure 4:
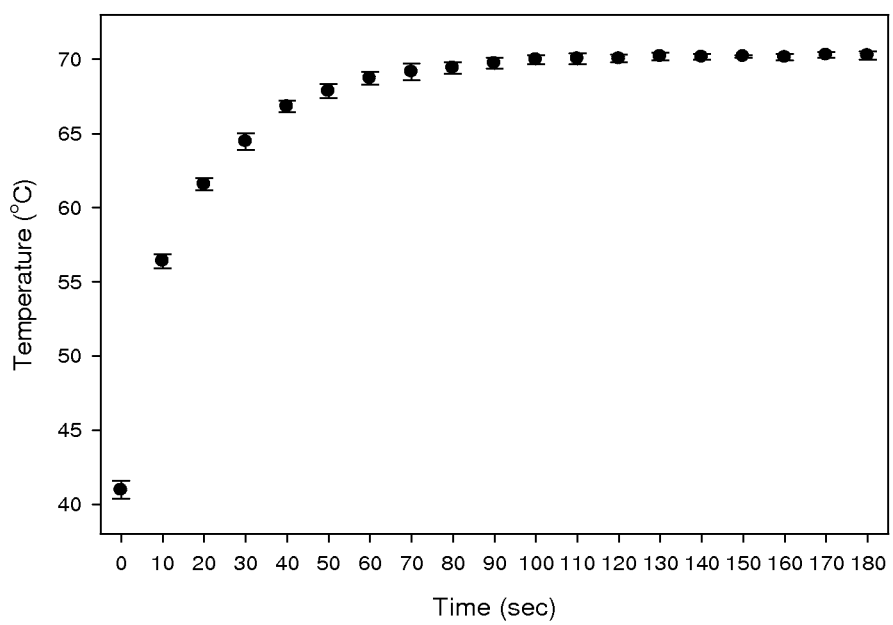
FIG. 4 is a graph of the temperature gradient at the tip of the sample capillary, according to an exemplary embodiment of the present invention.

With the DART source set to stand-by, 2 µL of the liquid samples were deposited into the melting point capillaries with the sampling assembly pulled out of the IMS. As soon as the liquid was deposited, the sample assembly was moved into the IMS desolation tube such that the gas transfer tube from the DART source extended 1.5 cm inside, and therefore the tip of the melting point capillary was 3.5 cm inside. The DART source was turned on and the data acquisition started. An 80 BK temperature probe connected to a multimeter (Fluke 179-True RMS, Everett, Wash.) was used to measure the temperature gradient at the tip of the sample capillary (FIG. 4). When the sample is placed inside the desolation tube and the DART source is turned on, there is a steep rise in the measured temperature up to 60 sec. From 60 sec until the end of the data acquisition (180 sec), the temperature remains fairly steady between 68.7 to 70.2° C.

Sequential data acquisitions were saved to monitor the detection response with respect to time for three minutes. For instance, a data file with the first 400 spectral sweeps took approximately 41 seconds to acquire. After the computer averages and saves this file (19 seconds) the next acquisition window started. Acquisition was repeated once more for a total of 3 averaged runs taking 1 minute each (3 minutes total). The same procedure was performed for the multiplexing experiments which investigated shorter averaging windows corresponding to the experiment performed for a more direct comparison with the conventional gating sequences. For all experiments, solvent blanks were run before each replicate to ensure a baseline signal was present. No reactive ion peaks were detected during blank or experimental runs.

Results and Discussion

With standalone IMS detection, the reduced mobility ($K_0$, in units of cm$^2$V$^{-1}$ s$^{-1}$) values can be calculated to help with identification of the ion species (Eq. 1):

$$K_0 = \frac{d}{Et} \frac{P}{760} \frac{273}{T} \quad \text{(Eq. 1)}$$

where d is the distance the ion drifts from the gate to the detector, t is the drift time of the ion, E is the electric field strength, P is the ambient pressure, and T is the drift tube temperature. The validity in these values is strengthened by MS detection for mass identification and reduced mobility tables have been constructed for various analytes although one single database has not been developed. It is possible that reported reduced mobility values may be wrong and thereby, incorrectly identify ions that are not mass analyzed. Errors can be due to several factors such as impurities, cluster formations, and/or thermal expansion or contraction of the drift tube, amongst others.

If a mass analyzer is not installed for IMS/MS detection, standard compounds with well investigated and stable reduced mobility values can be used to determine the reduced mobilities of unknowns under identical experimental conditions (Eq. 2):

$$K_0(\text{unknown}) = \frac{K_0(\text{standard})t_d(\text{standard})}{t_d(\text{unknown})} \quad \text{(Eq. 2)}$$

Although there is not one definitive IMS standard, experiments using 2,6-DtBP have shown the molecule to be reliable since it gives a single, stable protonated molecule signal under various experimental conditions with $K_0$=1.42 cm$^2$V$^{-1}$ s$^{-1}$. Using 2,6-DtBP standard in our system allowed for identification of the types of species formed during DART-IMS experiments.

Figure 5:
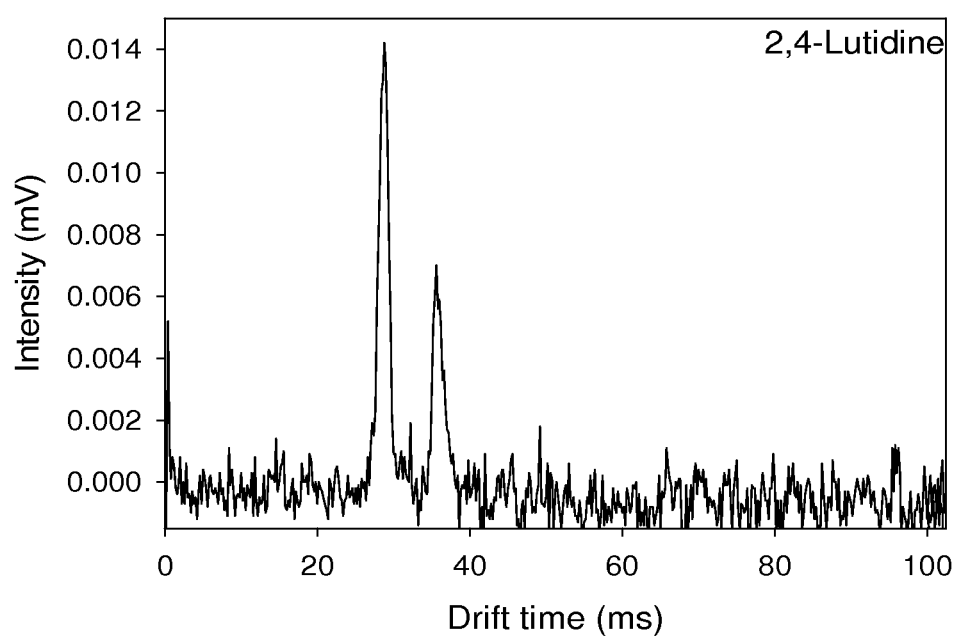
FIG. 5 is a graph of intensity versus drift time during an analysis of an exemplary embodiment of the present invention.
Figures 6A, 6B, 6C, 6D:
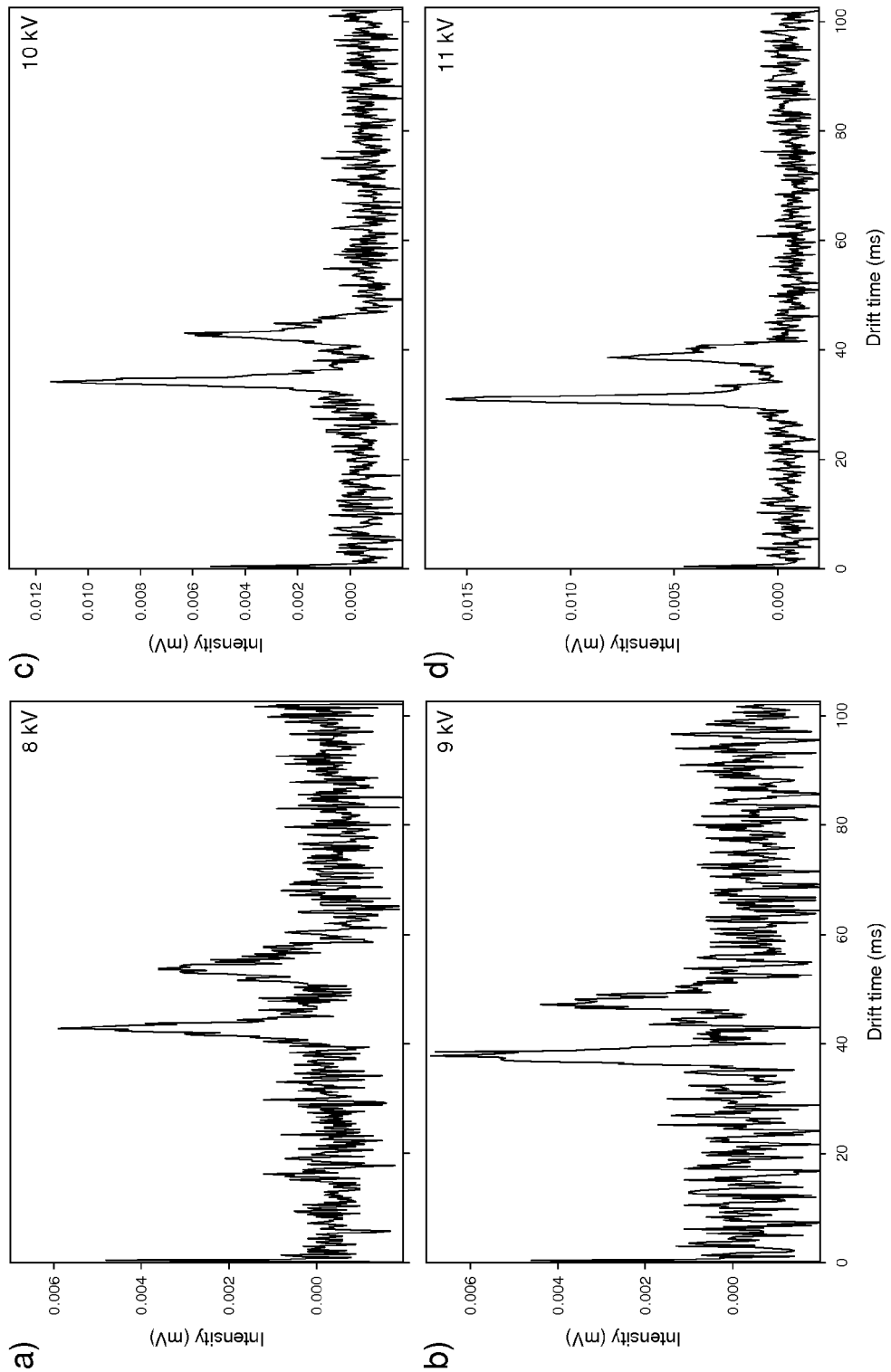
FIGS. 6a-6d are graphs of intensity versus drift time during an analysis of an exemplary embodiment of the present invention.

Initially, 2,4-lutidine was analyzed to assess the ion species formed during DART-IMS. At a field strength of 381.9 V cm$^{-1}$, two peaks were observed (FIG. 5). The two peaks at $t_d$=28.8 and 35.6 ms had $K_0$=1.73 and 1.40 cm$^2$V$^{-1}$ s$^{-1}$, respectively. Literature values for the protonated molecule and dimer of 2,4-lutidine are 1.95 and 1.43 cm$^2$V$^{-1}$s$^{-1}$, respectively. There is good correlation that the second peak is the protonated dimer of 2,4-lutidine, but the first observed peak has a reduced mobility value indicative of an ion size larger than the protonated molecule but smaller than the dimer. The first peak is likely a $[M+H]^+(H_2O)_n$ product ion of 2,4-lutidine. This cluster species has previously been observed with atmospheric pressure IMS. The protonated molecule cluster was probably formed from a reaction similar to Kebarle's water displacement mechanism (Eq. 3a) and the dimer was formed from subsequent reactions between these cluster species and neutrals (Eq: 3b):

(Eq. 3a)

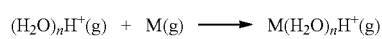

$$M(g) + M(H_2O)_n H^+(g) \xrightarrow{\text{heat}} (2M+H)^+(g) + (H_2O)_n \quad \text{(Eq. 3b)}$$

Additional experiments at other field strengths of 255, 286.5, 318.1, and 349.6 V cm$^{-1}$ showed the same species were formed indicating the generation of protonated clusters and dimers is likely occurring during ionization, and not from reactions during the ion drift time. (FIGS. 6a-6d).

In the lab, dimer formation of acetaminophen has been observed with DART analysis and other pharmaceuticals for identification of unknown active ingredients. Furthermore, cluster formation of atmospheric water vapor is always observed in the background of DART-MS experiments formed from Penning ionization, and solvent clusters have been suggested as having significant roles in ion formation via a transient microenvironment concept. Without declustering during travel within the first differentially-pumped stage of the mass spectrometer, cluster ions are likely to remain intact in DART-IMS.

The DART-IMS system was tested as a potential chemical agent monitoring system by monitoring three different toxic analytes: DMMP (Chemical Weapons Convention Schedule 2 substance used in the synthesis of Sarin) and 2-CEES (mustard gas analog) are both chemical warfare simulants, and a low vapor pressure chemical methamidophos (a harmful pesticide). The threshold of probable detection (TPD) of each analyte was assessed by monitoring its detection at five different concentration levels in replicates (n=8). The amount of successful detections (response SNR≧3) was fitted to a logistic function defined by (Eq. 4):

$$y = \frac{A_1 - A_2}{1 + (x/x_o)^p} + A_2 \quad \text{(Eq. 4)}$$

where, $A_1$ and $A_2$ are the lower and upper asymptote values, respectively, $x_0$ is the point of inflection and p is the rate of the curve steepness. The TPD is then selected at the point on the curve where the likelihood of detection is at least 95% (the level at which there is less than a 5% false negative rate). The TPD for DMMP, 2-CEES, and methamidophos were 11.81%, 1.13%, and 10.61 mM, respectively. These levels are high considering fmol solution concentrations using nanoESI-IMS have been performed on this instrument, and ppm and ppb levels are routinely detected with other IMS systems. Most likely, the relatively low temperatures and slow desorption time of the analytes from solution is the predominant cause. Work is underway to improve this problem.

Figures 7A, 7B, 7C:
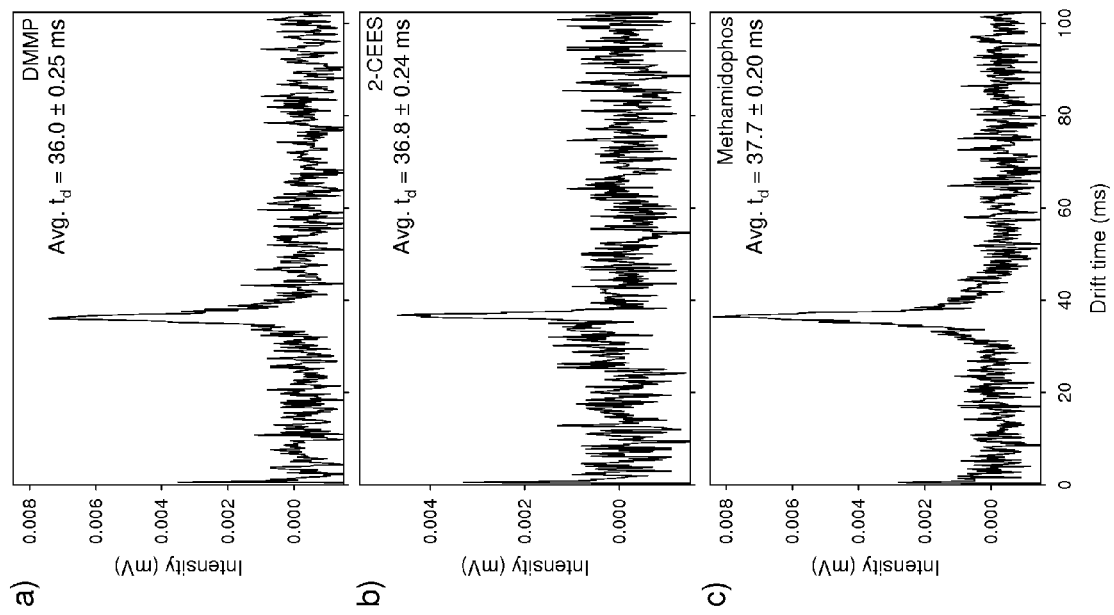
FIGS. 7a-7c are graphs of intensity versus drift time during an analysis of an exemplary embodiment of the present invention.

At the calculated TPD levels, 24 replicate experiments for each analyte resulted in positive detection for all trials (FIGS. 7a-7c). The average drift time, and reduced mobility for DMMP was 36.0±0.25 ms and 1.38±0.01 cm$^2$V$^{-1}$ s$^{-1}$, respectively. This matches the literature value of the protonated dimer of DMMP. The average drift time and reduced mobility for 2-CEES was 36.8±0.24 ms and 1.35±0.01 cm$^2$V$^{-1}$ s$^{-1}$, respectively. The average drift time and reduced mobility for methamidophos was 37.7±0.2 ms and 1.32±0.01 cm$^2$V$^{-1}$s$^{-1}$, respectively. There was no literature reduced mobility values found for both 2-CEES and methamidophos, however their reduced mobilities are very close in value to the established protonated dimer reduced mobility of DMMP.

Figure 8:
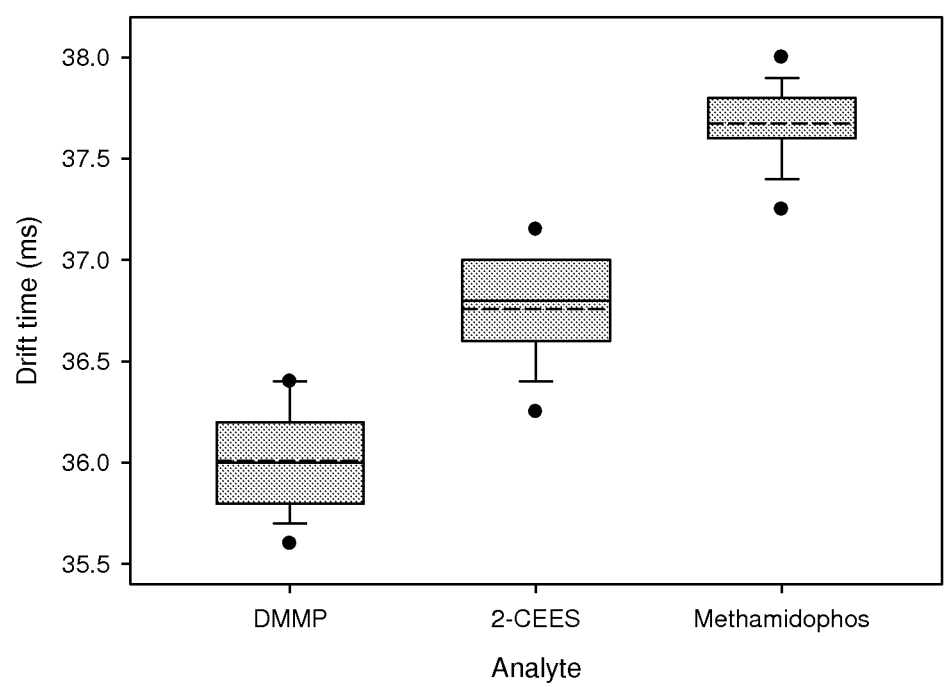
FIG. 8 is a graph of the mean, median, lower, upper and interquartiles of each analyte tested plotted in a box plot, according to an exemplary embodiment of the present invention.

To ensure that the detected species are indeed different and not contaminants in the system, the mean, median, lower, upper and interquartiles of each analyte were plotted in a box plot and were found to be exclusive of each other (FIG. 8). The high outlier for DMMP is on the border with the lower quartile range marker of 2-CEES and the lower outlier of 2-CEES overlaps with the upper quartile range of DMMP, but these points would not significantly change the identification based on all the results. Therefore, the results suggest that the detected species of 2-CEES and methamidophos are distinct ions and probably dimers although without mass identification or literature reduced mobility values to compare to, no definitive identification can be made at this time.

For the previous experiments, a traditional pulsed IMS approach was used on the ion beam to create a discrete ion packet. Data was acquired in what is commonly called signal averaging mode which carries a drawback: only when the ion gate is closed (no pulsing) will ions be detected. In addition, as detection is occurring any new ions formed from the ionization source are lost due to neutralization against the closed ion gate. For instance, in the current set-up the ion gate pulse width was 400 μs (one element) and each run lasted 102.4 ms (a 256 element sequence). The maximum theoretical duty cycle (the temporal ratio of the pulse width to experiment length) is ~0.4%. In this scenario, >99% of the ions formed will never be analyzed. One approach to mitigate low duty cycle would be to increase the gate pulse width. Lengthening the width may improve the total amount of ions and therefore, the sensitivity of the experiment (if noise is held constant), but there would be a loss of resolving power.

Multiplexing with IMS aims to increase the duty cycle of the analysis and improve the sensitivity (signal-to-noise ratio) and potentially reduce the time required to conduct the experiment without changing anything of the physical instrument itself. Multiplexed DTIMS injects multiple packets of ions successively throughout the sequence. The immediately recorded spectrum is convoluted, and appears as nothing but noise. However, by knowing the gate pulse widths, the sequence of the openings, and the ions' arrival times, one can deconvolute the signal and generate a clean spectrum. For example, in a traditional IMS experiment, the gate would open in the beginning of the run and then close until all ions were detected. If the sequence was 16 elements in length, only the first element would represent an open gate (FIG. 9a). Here, the duty cycle would be 6.25%. A multiplexed approach would add more injections to the sequence to increase the total amount of ions sampled. Ions could be injected for 2, 4 or 8 elements selected randomly along the 16-element sequence representing duty cycles of 12.5, 25 and 50%, respectively (FIGS. 9b-9d). The total number of combinations of injections is dependent on the length of the sequence (n) and the amount of open injections (r) defined by (Eq. 5):

$$\text{Combinations} = \frac{n!}{r!(n-r)!} \quad \text{(Eq. 5)}$$

For the previous examples, there are 120, 1820, and 12870 different sequences possible for the 2, 4, and 8 multiplexed injections for a 16 element sequence, respectively.

Figures 10A, 10B, 10C, 10D, 10E, 10F:
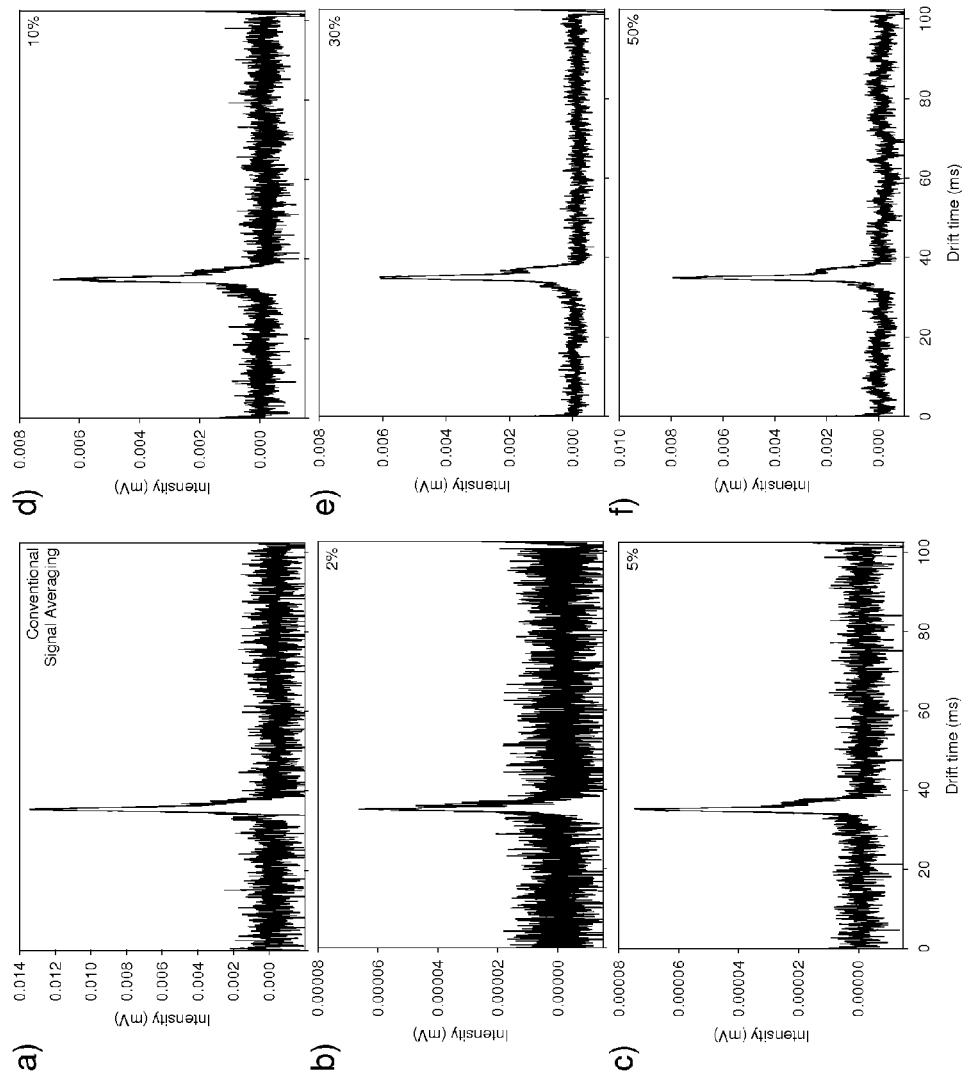
FIGS. 10a-10f are graphs of intensity versus drift time during an analysis of an exemplary embodiment of the present invention.

In order to improve the detection capabilities and speed of the analysis of the DART-IMS platform, digital multiplexed IMS was investigated. Only one analyte, DMMP, was investigated since there was positive identification of the detected species formed during conventional signal averaging mode analysis. Conventional signal averaging of 400 runs at a ~0.4% duty cycle (400 μs gate pulse and 50 μs acquisition windows) had a signal-to-noise ratio of 4.2 (FIG. 10a). For 2, 5 and 50% duty cycles, the signal-to-noise ratios were 2.5, 4.2, and 4.2 respectively (FIGS. 10b, c and f). The lack of improvement is probably due to the particular sequence selected to run the experiment. The increase in noise and lack of improvement of the higher duty-cycle trials compared to the conventional signal averaging spectrum are a common result of the specific distribution of gating events (when the ion gate is open with respect to the total sequence).

Figures 11A, 11B, 11C, 11D, 11E, 11F:
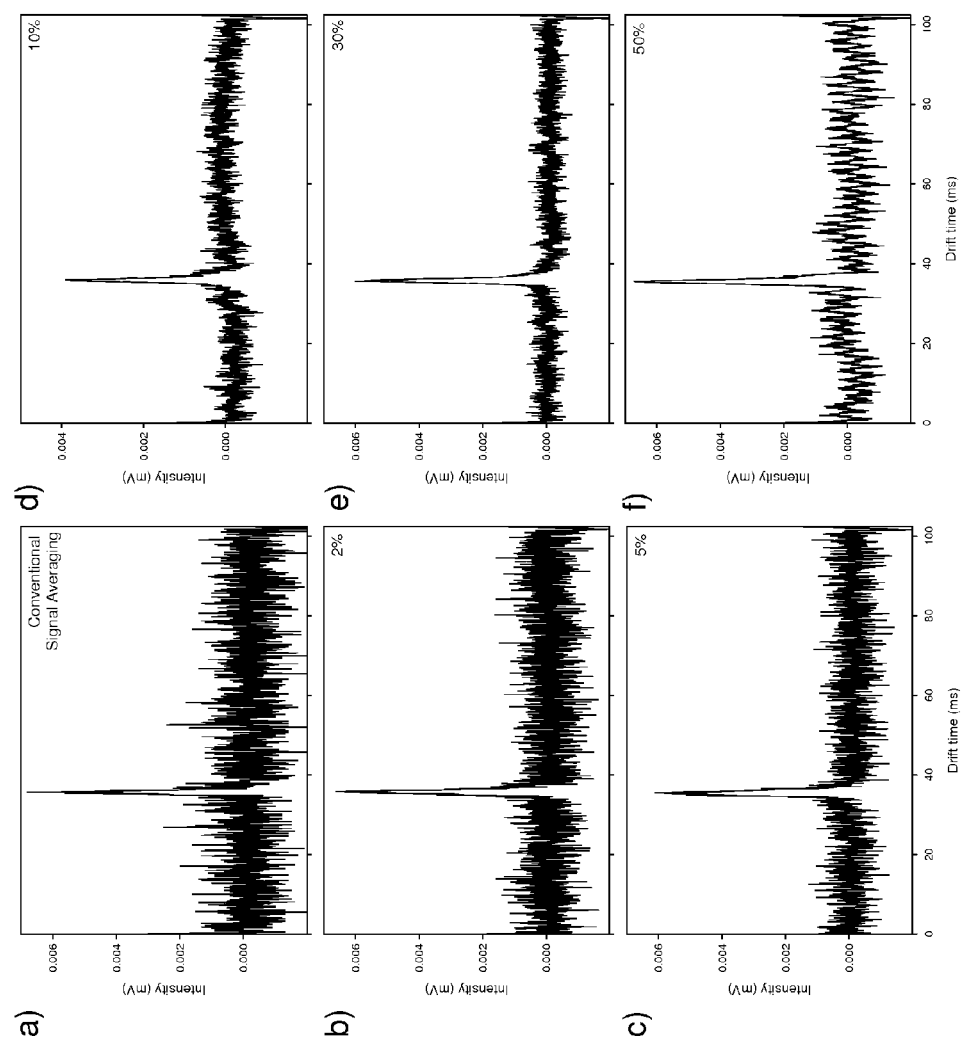
FIGS. 11a-11f are graphs of intensity versus drift time during an analysis of an exemplary embodiment of the present invention.
Figures 12A, 12B:
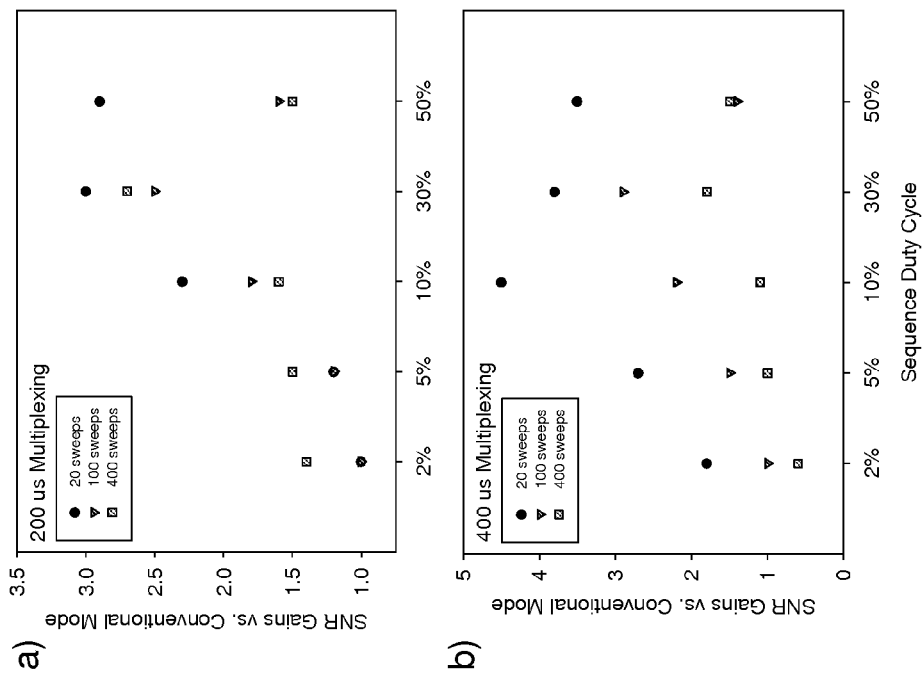
FIGS. 12a-12b are graphs of multiplexed gains of the 200 and 400 μs gates for all sweep averages over conventional mode, according to an exemplary embodiment of the present invention.

In the case of the 2% spectrum, this is one sequence of more than $>8.8 \cdot 10^9$ possible combinations. Other spectra recorded at 10 and 30% duty cycles showed an improved values of signal-to-noise ratios of 4.6 and 7.6, respectively (FIGS. 10d and e). The same experiment but with a 200 µs gate and 50 µs acquisition windows for signal averaging mode has a signal-to-noise ratio of 2.2 which is below the minimum standard of chemical detection at a signal-to-noise ratio of 3 (FIG. 11a). Conversely, at 2, 5, 10, 30, and 50% duty cycle sequences at 400 sweeps averaged should improved signal-to-noise ratios of 3, 3.2, 3.5, 6 and 3.3, respectively (FIG. 11). In addition to the 400 sweep average of runs conducted in all the examples so far, additional experiments were performed at 20 and 100 sweep averages. The multiplexed gains of the 200 and 400 µs gates for all sweep averages over conventional mode are shown in FIG. 12. The greater signal-to-noise ratio gains of the lower spectral sweep averages are due to two factors. First, traditional signal averaging experiments have too much noise in the baseline and prevent the observation of any signal with only 20 or 100 sweep averages. As a result, any signal observed for the multiplexed sequences will be higher than the signal averaging experiments and this is shown at its maximum at both the 20 sweep averages of the 30% 200 µs and 10% 400 µs signal-to-noise ratio gains of 3 and 4.5, respectively (FIGS. 12a and 12b).

For comparison purposes, a more traditional 50% duty cycle method was probed utilizing Hadamard Transform (HT) sequences.

Figures 13A, 13B, 13C, 13D, 13E, 13F:
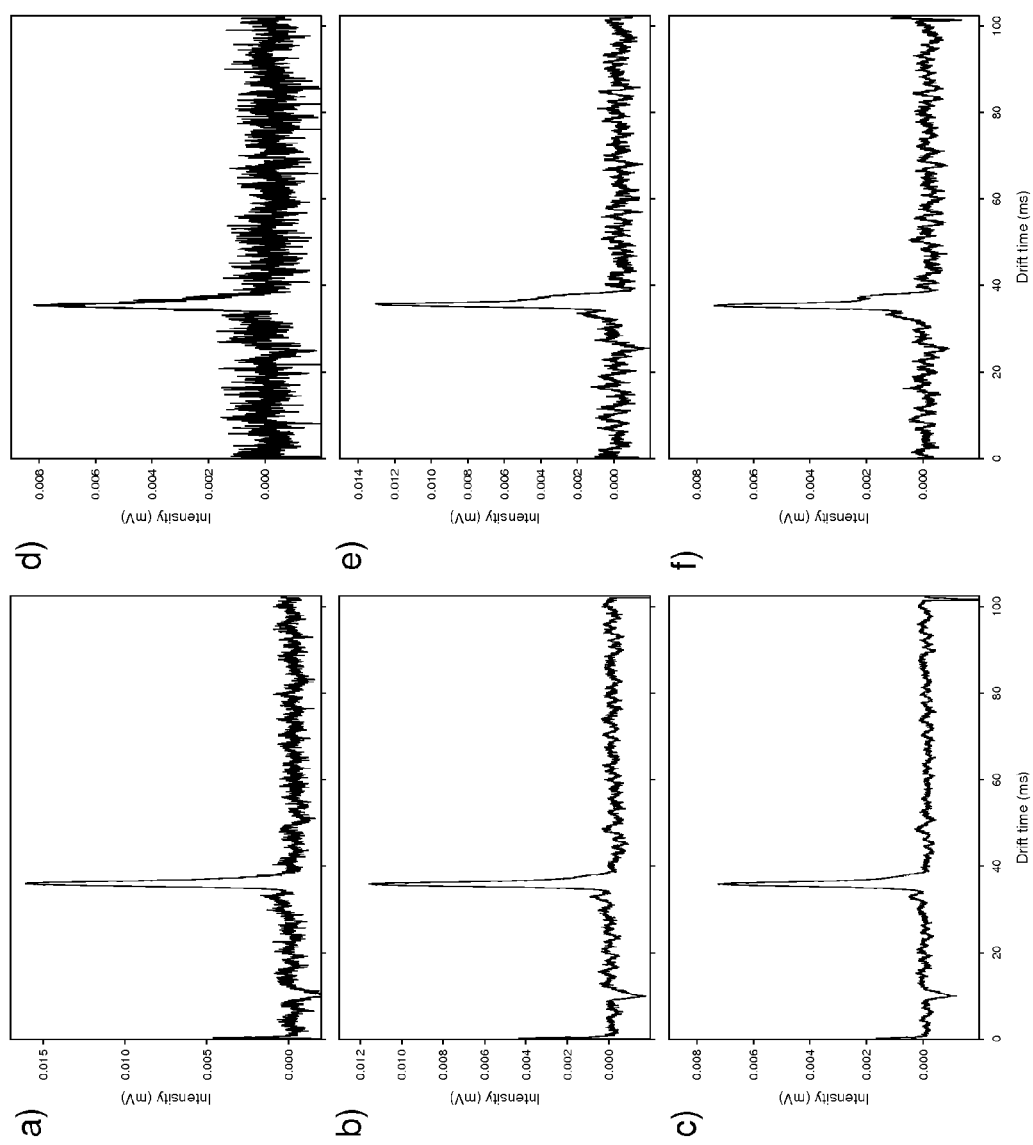
FIGS. 13a-13f are graphs of intensity versus drift time during an analysis of an exemplary embodiment of the present invention.

For both 200 µs and 400 µs gate widths at 20, 100, and 400 sweep averaged runs HT sequences showed signal-to-noise ratio gains over conventional signal averaging experiments (FIG. 13). The greatest gains correlated to 20 sweep averaged runs at 200 µs gates with a gain of 8 over conventional mode (FIG. 13a). However, accompanying these gains were spectral defects in the acquired spectra. These defects were most noticeable with the 200 µs gates appearing as negative peaks at drift times of 10.45, 9.95, and 10.05 ms for 20, 100, and 400 sweeps averaged (FIG. 13a, b and c). Smaller defect peaks were observed with 400 µs gates at drift times of 24.95, 25.30 and 25.35 ms for 20, 100, and 400 sweeps averaged, respectively (FIG. 13d, e and f). Defect peaks are due to imperfect ion packet shapes within the drift tube created by the mathematical properties of Hadamard-type sequences. All these defects manifest themselves negatively as ghost or echo peaks. These defects may ultimately result in false-positive or false-negative detections.

The experiments above provide the first results of an ambient plasma ion source coupled to a drift tube atmospheric pressure ion mobility spectrometer, and show the ability to detect and identify toxic chemicals including chemical warfare simulants and low vapor pressure chemicals with statistically significant results. Digital multiplexing techniques were utilized leading to improved signal-to-noise ratio gains over conventional signal averaging experiments, and without artifacts as with Hadamard multiplexing approaches.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. A sample analyzing system, comprising:
   a plasma ionization source configured to ionize an analyte sample under ambient pressure;
   an ion mobility spectrometer configured to operate under ambient pressure, wherein the ion mobility spectrometer comprises an inlet, an ionization region, a ion separation region, and a detector, arranged such that the ionization region is downstream of the inlet, the ion separation region is downstream of the ionization region, and the detector is downstream of the ion separation region; and
   a sample transport assembly configured to transport the analyte sample through the inlet of the ion mobility spectrometer and to the ionization region, wherein the sample transport assembly is in physical communication with the plasma ionization source;
   wherein ionization of the analyte sample occurs in-situ within the ionization region of the ion mobility spectrometer; and
   wherein an electric field at the inlet of the ion mobility spectrometer is greater than an electric field produced by the plasma ionization source when both the ion mobility spectrometer and the plasma ionization source are activated.

2. The sample analyzing system of claim 1, wherein the plasma ionization source comprises a neutral ionization source.

3. The sample analyzing system of claim 1, wherein the plasma ionization source is a direct analysis in real time ionization source.

4. The sample analyzing system of claim 1, wherein the sample transport assembly comprises:
   a sample platform configured to hold the analyte sample; and
   a tube comprising a first end comprising an inlet and a second end comprising an outlet, wherein the first end of the tube is in physical communication with the plasma ionization source, and wherein the second end of the tube is in physical communication with the sample platform.

5. The sample analyzing system of claim 4, wherein the sample platform is porous, and wherein the porous sample platform facilitates transport of a liquid, gaseous, or aerosol analyte sample into the ionization region of the ion mobility spectrometer.

6. The sample analyzing system of claim 5, wherein the porous sample platform comprises a sorbent material for holding the liquid, gaseous, or aerosol analyte sample.

7. The sample analyzing system of claim 5, wherein the porous sample platform is at least partially formed from an electrically conductive material.

8. The sample analyzing system of claim 7, wherein the at least partially electrically conductive porous sample platform is positioned at the inlet of the ion mobility spectrometer effective to permit the electric field at the inlet of the ion mobility spectrometer to travel through the electrically conductive porous sample platform such that the inlet comprises at least a portion of the ionization region.

9. A method of analyzing a sample, the method comprising:

providing an ion mobility spectrometer comprising an inlet, an ionization region, a ion separation region, and a detector, arranged such that the ionization region is downstream of the inlet, the ion separation region is downstream of the ionization region, and the detector is downstream of the ion separation region;

introducing an analyte sample into the ionizing region of the ion mobility spectrometer;

ionizing the analyte sample in-situ within the ionizing region of the ion mobility spectrometer, wherein the ionizing occurs under ambient pressure via a plasma ionization source;

separating ions of the ionized analyte sample under ambient pressure within the ion separation region; and detecting at least a portion of the ions under ambient pressure with the detector of the ion mobility spectrometer;

wherein an electric field at the inlet of the ion mobility spectrometer is greater than an electric field produced by the plasma ionization source when both the ion mobility spectrometer and the plasma ionization source are activated; and wherein both the plasma ionization source and the ion mobility spectrometer are not activated when the analyte sample is introduced into the ionizing region of the ion mobility spectrometer.

10. The method of analyzing the sample of claim 9, wherein the introducing is accomplished using a sample transport assembly, wherein the sample transport assembly is in physical communication with the plasma ionization source.

11. The method of analyzing the sample of claim 10, wherein the sample transport assembly comprises:
a sample platform configured to hold the analyte sample; and
a tube comprising a first end comprising an inlet and a second end comprising an outlet, wherein the first end of the tube is in physical communication with the plasma ionization source, and wherein the second end of the tube is in physical communication with the sample platform.

12. The method of analyzing the sample of claim 11, wherein the sample platform is porous, and wherein the porous sample platform facilitates transport of a liquid, gaseous, or aerosol analyte sample into the ionization region of the ion mobility spectrometer.

13. The method of analyzing the sample of claim 12, wherein the porous sample platform comprises a sorbent material for holding the liquid, gaseous, or aerosol analyte sample.

14. The method of analyzing the sample of claim 13, wherein the porous sample platform is at least partially formed form an electrically conductive material.

15. The method of analyzing the sample of claim 14, wherein the at least partially electrically conductive porous sample platform is positioned at the inlet of the ion mobility spectrometer effective to permit the electric field at the inlet of the ion mobility spectrometer to travel through the electrically conductive porous sample platform such that the inlet comprises at least a portion of the ionization region.

16. The method of analyzing the sample of claim 9, wherein the plasma ionization source comprises a neutral metastable ionization source.

17. The method of analyzing the sample of claim 9, wherein the plasma ionization source is a direct analysis in real time ionization source.

18. The method of analyzing the sample of claim 9, wherein the plasma ionization source is a flowing atmospheric pressure afterglow ionization source.

19. The method of analyzing the sample of claim 9, wherein the plasma ionization source is a low temperature plasma probe ionization source.

20. The method of analyzing the sample of claim 9, wherein the analyte sample comprises more than one chemical constituent, such that ionizing the analyte sample comprises ionizing each of the more than one chemical constituents, separating ions of the ionized analyte sample comprises separating ions of each of the more than one chemical constituents, and detecting at least the portion of the ions comprises detecting at least a portion of the ions of each of the more than one ionized chemical constituents.

21. The method of analyzing the sample of claim 20, wherein each of the more than one chemical constituents is ionized at a different time.

22. The method of analyzing the sample of claim 21, wherein the at least a portion each of the more than one ionized chemical constituents are detected at a different time.

23. An ambient analyte identification process comprising:
providing an ion mobility spectrometer with an inlet and a reaction region in a drift tube;
applying an electric field at the inlet of the ion mobility spectrometer;
placing a sample through the inlet, and into the reaction region of the ion mobility spectrometer; and
ionizing the sample in the reaction region of the ion mobility spectrometer with an ambient plasma ionization source;
wherein ionization of the sample occurs in-situ within the electric field gradient of the ion mobility spectrometer;
wherein the ions travel through the drift tube which has the applied electric field and a carrier buffer gas that opposes the ions' motion; and
wherein a detector in proximity to a distal end of the drift tube can distinguish different analyte species based on an ions' mass, charge, size and shape, such that the migration time through the tube is characteristic of different ions.

24. The ambient sample analysis process of claim 23, wherein ionization of the sample is provided by an ambient plasma ionization source.

25. The ambient sample analysis process of claim 23, wherein placing a sample through the inlet, and into the reaction region of the ion mobility spectrometer comprises mounting the sample and a reagent gas transfer tube on a movement system, wherein the reagent gas transfer tube both holds the sample, and hydro-dynamically focuses the gas plume from the ambient plasma ionization source onto the sample, facilitating efficient ionization of surface bound species.

26. The ambient sample analysis process of claim 25, wherein the movement system comprises a rail system external the ion mobility spectrometer allowing for safe, repeatable and reproducible placement of the sample into the reaction region of the ion mobility spectrometer.

* * * * *